US008562804B2

(12) United States Patent
Santiago et al.

(10) Patent No.: US 8,562,804 B2
(45) Date of Patent: *Oct. 22, 2013

(54) FLUORESCENT FINGER PRINTS FOR INDIRECT DETECTION IN ISOTACHOPHORESIS

(75) Inventors: Juan G. Santiago, Stanford, CA (US); Moran Bercovici, Santa Clara, CA (US); Govind V. Kaigala, Horgen (CH); Robert D. Chambers, Enfield, NH (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 190 days.

This patent is subject to a terminal disclaimer.

(21) Appl. No.: 13/134,165

(22) Filed: May 31, 2011

(65) Prior Publication Data

US 2012/0152746 A1   Jun. 21, 2012

Related U.S. Application Data

(63) Continuation-in-part of application No. 11/880,479, filed on Jul. 20, 2007, now Pat. No. 7,951,278.

(60) Provisional application No. 61/462,900, filed on Feb. 8, 2011, provisional application No. 60/832,332, filed on Jul. 20, 2006.

(51) Int. Cl.
*G01N 27/26* (2006.01)
*G01N 27/447* (2006.01)
*B01D 57/02* (2006.01)

(52) U.S. Cl.
USPC .......................................... 204/549; 204/645

(58) Field of Classification Search
USPC ............................................. 204/549, 645
See application file for complete search history.

(56) References Cited

U.S. PATENT DOCUMENTS

| 3,869,365 A | 3/1975 | Sunden |
| 3,948,753 A | 4/1976 | Arlinger |

(Continued)

FOREIGN PATENT DOCUMENTS

| EP | 1742057 | 1/2007 |
| EP | 2340122 A1 | 7/2011 |

OTHER PUBLICATIONS

Khurana et al., "Preconcentration, separation, and indirect detection of nonfluorescent analytes using fluorescent mobility markers", 2008, pp. 279-286, Anal. Chem. v80.

(Continued)

*Primary Examiner* — J. Christopher Ball
*Assistant Examiner* — Jennifer Dieterle
(74) *Attorney, Agent, or Firm* — Lumen Patent Firm

(57) ABSTRACT

Indirect detection and/or identification of analytes by ITP can be enhanced by adding a mixture of labeled carrier ampholytes (CAs) to the sample to provide a continuous range of mobility markers. Each analyte can be detected and quantified by corresponding gaps in the CA signal. This approach does not require a priori choice of fluorophores and can be readily applied (without extensive and specific design) to a wide range of analytes. Analyte identification can be expedited by computing a normalized signal integral (NSI) from the CA signals. Empirical calibrations can relate the NSI to effective mobility. Effective mobility results under two or more different pH conditions can be used to determine analyte pKa and fully ionized mobility, which are analyte properties that can facilitate analyte identification.

20 Claims, 8 Drawing Sheets

(56) References Cited

U.S. PATENT DOCUMENTS

| | | | |
|---|---|---|---|
| 4,897,169 | A | 1/1990 | Bier et al. |
| 5,447,612 | A | 9/1995 | Bier et al. |
| 5,464,515 | A | 11/1995 | Bellon |
| 5,817,225 | A | 10/1998 | Hinton |
| 5,939,291 | A | 8/1999 | Loewy et al. |
| 6,685,813 | B2 | 2/2004 | Williams et al. |
| 6,780,584 | B1 | 8/2004 | Edman et al. |
| 6,818,113 | B2 | 11/2004 | Williams et al. |
| 6,934,836 | B2 | 8/2005 | Strand et al. |
| 7,214,299 | B2 | 5/2007 | Armstrong |
| 7,223,325 | B2 | 5/2007 | Landers et al. |
| 7,316,771 | B2 | 1/2008 | Weber |
| 7,371,533 | B2 | 5/2008 | Slater et al. |
| 7,399,394 | B2 | 7/2008 | Weber |
| 7,473,551 | B2 | 1/2009 | Warthoe |
| 7,494,577 | B2 | 2/2009 | Williams et al. |
| 7,517,442 | B1 | 4/2009 | Champagne |
| 7,635,563 | B2 | 12/2009 | Horvitz et al. |
| 7,951,278 | B2 * | 5/2011 | Santiago et al. ............... 204/549 |
| 8,017,408 | B2 | 9/2011 | Meinhart et al. |
| 8,021,531 | B2 | 9/2011 | Park et al. |
| 8,133,371 | B2 | 3/2012 | Marziali et al. |
| 8,277,628 | B2 | 10/2012 | Ronaghi et al. |
| 8,394,251 | B2 | 3/2013 | Santiago et al. |
| 2004/0031683 | A1 | 2/2004 | Eipel et al. |
| 2005/0121324 | A1 | 6/2005 | Park et al. |
| 2005/0133370 | A1 | 6/2005 | Park et al. |
| 2005/0170362 | A1 | 8/2005 | Wada et al. |
| 2006/0042948 | A1 | 3/2006 | Santiago et al. |
| 2006/0078998 | A1 | 4/2006 | Puskas et al. |
| 2008/0020386 | A1 | 1/2008 | Chen et al. |
| 2008/0021674 | A1 | 1/2008 | Puskas |
| 2008/0156080 | A1 | 7/2008 | Balgley |
| 2008/0166770 | A1 | 7/2008 | Morita et al. |
| 2008/0197019 | A1 | 8/2008 | Santiago et al. |
| 2009/0178929 | A1 | 7/2009 | Broer et al. |
| 2010/0116657 | A1 | 5/2010 | Fiering et al. |
| 2010/0224494 | A1 | 9/2010 | Chambers et al. |
| 2010/0261612 | A1 | 10/2010 | Young |
| 2010/0270157 | A1 | 10/2010 | Kurosawa et al. |
| 2010/0323913 | A1 | 12/2010 | Young et al. |
| 2011/0024296 | A1 | 2/2011 | Park et al. |
| 2011/0036718 | A1 | 2/2011 | Jung et al. |
| 2011/0174624 | A1 | 7/2011 | Weber |
| 2011/0220499 | A1 | 9/2011 | Chambers et al. |
| 2011/0297546 | A1 | 12/2011 | Schoch |
| 2012/0061242 | A1 | 3/2012 | Santiago et al. |
| 2012/0152746 | A1 | 6/2012 | Santiago et al. |
| 2012/0160689 | A1 | 6/2012 | Utz et al. |
| 2012/0175258 | A1 | 7/2012 | Mariella, Jr. |

OTHER PUBLICATIONS

Schafer-Neilsen et al., "Separation of macromolecules in isotachophoresis systems involving single or multiple counterions", 1980, pp. 97-128, Journal of Biochemical and Biophysical Methods v3.

Gohring, et al. The scaffold/matrix attachment region binding protein hnRNP-U (SAF-A) is directly bound to chromosomal DNA in vivo: a chemical cross-linking study. Biochemistry. Jul. 8, 1997;36(27):8276-83.

Morio, et al. Quantitative analysis of trifluoroacetate in the urine and blood by isotachophoresis. Anesthesiology. Jul. 1980;53(1):56-9.

* cited by examiner

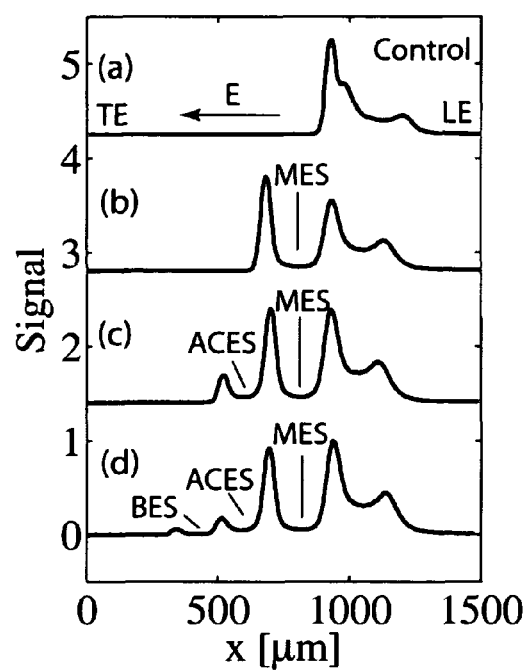
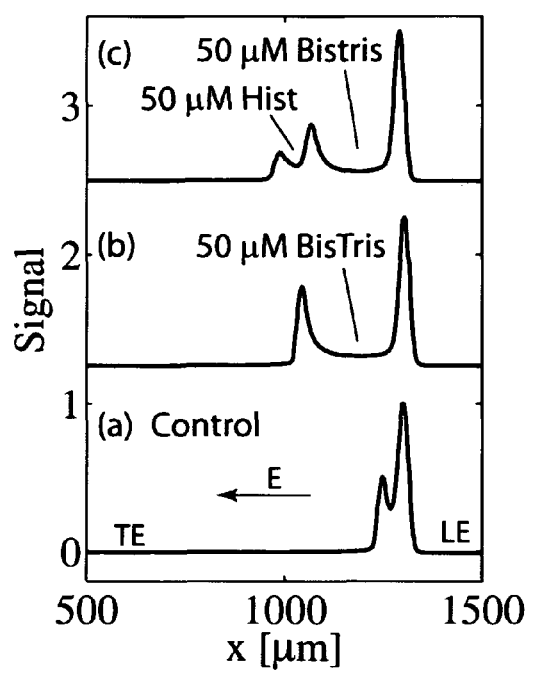
Fig. 2
Fig. 3

FLUORESCENT FINGER PRINTS FOR INDIRECT DETECTION IN ISOTACHOPHORESIS

CROSS REFERENCE TO RELATED APPLICATIONS

This application claims the benefit of U.S. provisional patent application 61/462,900, filed on Feb. 8, 2011, entitled "Fluorescent finger prints for indirect detection in isotachophoresis", and hereby incorporated by reference in its entirety. This application is also a continuation in part of U.S. application Ser. No. 11/880,479, filed on Jul. 20, 2007, entitled "Method of detecting directly undetectable analytes using directly detectable spacer molecules", now U.S. Pat. No. 7,951,278, and hereby incorporated by reference in its entirety. Application Ser. No. 11/880,479 claims the benefit of U.S. provisional patent application 60/832,332, filed on Jul. 20, 2006, entitled "Directly detectable spacers for indirect detection of analytes", and hereby incorporated by reference in its entirety.

GOVERNMENT SPONSORSHIP

This invention was made with Government support under contract number N66001-09-1-2007 awarded by the Defense Advanced Research Projects Agency (DARPA). The Government has certain rights in this invention.

FIELD OF THE INVENTION

This invention relates to sample analysis based on isotachophoresis.

BACKGROUND

Environmental monitoring efforts and water quality assessment in particular would benefit from widely available and inexpensive chemical assays and sensor technologies. Gas and liquid chromatography methods, and their coupling to mass spectrometry, are currently standard methods suggested by the US environmental protection agency (EPA) for detection of chemical toxins in drinking water. While these methods are considered sufficiently sensitive and accurate, their use is mostly confined to laboratory settings due to their size, weight, power requirement, peripheral equipment, cost, and sample preparation steps. There is a need for detection techniques which are cost-effective, sensitive, and portable.

One approach towards widespread toxin detection is the miniaturization of traditional chromatography systems. While there have been efforts which significantly reduce size and weight, scaling down and integrating the essential system components remains a challenge. Much of the work is focused on implementation of an efficient stationary phase in microstructures, and in miniaturization of pressure sources, pumps, and valves.

An alternative approach to realizing low-cost and portable toxins detection is developing novel assays which have increased functionality, avoid complex sample preparation (e.g., labeling), and are compatible with inexpensive system architectures and sensitive detection methods. Fluorescence based detection is the most sensitive method for on-chip applications, but typically requires autofluorescent analytes (a property that is not possessed by most toxins of interest) or fluorescent labeling (e.g. using immunoassays).

Recently, several fluorescence-based detection methods based on isotachophoresis (ITP) have been proposed. In ITP, sample ions simultaneously focus and separate according to their electrophoretic mobilities between a leading electrolyte (LE) and trailing electrolytes (TE). This creates purified, high-concentration, adjacent zones electromigrating at a uniform velocity. However, previous work on ITP analysis often relied on ad hoc assay design. For example, it may be necessary to include a labeled marker species in the assay that has an effective mobility between the effective mobilities of two analytes of interest. In such cases, a priori knowledge of analyte properties (i.e., effective mobilities) is needed to select an appropriate marker species.

It would be an advance in the art to provide an assay that does not require such a priori knowledge of analyte properties.

SUMMARY

Indirect detection and/or identification of analytes by ITP can be enhanced by adding a mixture of labeled carrier ampholytes (CAs) to the sample to provide a continuous range of mobility markers. Each analyte can be detected and quantified by corresponding gaps in the CA signal. This approach does not require a priori choice of fluorophores and can be readily applied (without extensive and specific design) to a wide range of analytes.

An exemplary analysis method starts with a sample including one or more analytes to be analyzed. A carrier ampholyte (CA) mixture is added to the sample. The CA mixture includes numerous labeled species having a range of isoelectric points. Isotachophoresis (ITP) is then performed on the combined CA mixture and sample to provide an ITP separation. Signals from the labeled species (of the CA mixture) in the ITP separation are measured. Analytes can be detected and/or identified based on analysis of the measured CA signals. As a simple example, a focused analyte will tend to displace CA species from the region where the analyte focuses, thereby decreasing the CA signal from that part of the separation.

Carrier ampholytes (CA) are mixtures of different species, typically artificially synthesized polypeptides. They are typically used in isoelectric focusing (IEF) to produce a stationary pH gradient. Commercially available CA mixtures contain between a few hundred to a few thousands (more exact estimates are typically proprietary information) different species, which possess a range of isoelectric points (pI). A typical example of such a product is ZOOM® carrier ampholytes pH 3-10, presently sold by Invitrogen. Commercial CA mixtures are typically identified by a pH range of the isoelectric points of the included species. In the preceding example, this range of isoelectric points is from pH 3 to pH 10.

Surprisingly, we have found that such CA mixtures can be useful in assays, even if their detailed composition is not known (i.e., it suffices to know the pH range, which is typically supplied by the vendor). Alternatively, it is also possible to practice the present approach by formulating a mixture of species having a range of electrophoretic mobilities, rather than purchasing it. In such cases, it is expected that 10 or more different species would be used, and that these species would cover a range of effective electrophoretic mobilities from $\mu min$ to $\mu max$, where $\mu max - \mu min \geq 10E-9$ $m^2/(Vs)$. The labeled species in the CA mixture can be amphoteric, cationic and/or anionic. As will be seen below, it is preferred for the species in the CA mixture to have a range of properties that extends past the range of properties of the analytes (e.g., the CA mixture preferably has an effective mobility range that covers the effective mobility range of the analytes). In this sense, the CA mixture is preferably amphoteric with respect to the analytes, even if the species in the CA mixture are all anionic or all cationic.

The species in the CA mixture can be labeled with any kind or combination of labels, including but not limited to: fluorescent labels, electrochemical labels, UV absorbance labels, thermo-optical labels and/or radioactive labels. Preferably, fluorescent labels are employed, and the resulting technique is often referred to as an FCA (fluorescent carrier ampholytes) assay below. The ITP separation can be an anionic ITP separation or a cationic ITP separation. Practice of the invention does not depend critically on details of the labeling, or on details of how signals from the labeled CA species are detected.

The analytes are typically not labeled. Thus, this is an indirect detection approach, where signals from the CA species are the quantities that are measured, and analytes are detected and/or identified by how they affect the CA signals. Thus, this approach does not rely on measuring any signals that are directly from the analytes. Such indirect detection advantageously avoids substantial problems associated with labeling analytes. For example, often one would need to know what the analyte is in order to select a suitable label, but such a priori knowledge is usually unavailable. In cases where the analyte itself can provide a signal (e.g., FCA of an analyte that is inherently fluorescent), it is important to label the CA species such that the CA signal can be distinguished from any analyte signals. For fluorescent labeling of the CAs, the CA labels can be selected to fluoresce at different wavelengths from any analyte that may be in the sample.

As described in greater detail below, it is often preferred to perform the ITP separation in a channel having a wide part connected to a narrow part, where the wide part has a larger cross-section area than the narrow part. In such a configuration, the CA signals are measured at one or more points in the narrow part of the channel. As described below, this approach tends to increase measurement sensitivity, although there are trade offs to be aware of (such as increased measurement time).

Analyte identification can be expedited by computing a normalized signal integral (NSI). The NSI is basically an integrated intensity of the CA signal from one end of the ITP separation to the other. Empirical calibrations can be performed that relate NSI to effective mobility (for fixed CA mixture and fixed ITP LE and TE). Such empirical calibrations do not require knowledge of the CA mixture composition. Instead, several species having known properties can be characterized by FCA assay to provide this calibration.

Calibrations can be established for two or more different ITP conditions (e.g., two or more different pH values). Characterizing the same sample in these two or more different ITP conditions can allow the fully ionized mobility and pKa of a single analyte in the sample to be determined from the measurements of effective mobility obtained by the NSI calibrations.

Even in cases where an NSI calibration is not performed, it may still be helpful to add one or more species having known properties to the sample in order to provide an internal reference for effective mobility of the one or more analytes. Preferably, these added species are labeled to be distinguishable from the CA background signal.

This analysis approach can be extended to provide 2-D data. For example, the sample can be assayed at several different pH values to provide a 2-D pattern of CA signals vs. pH. Such patterns may help with analyte identification (e.g., by pattern matching to a library of known 2-D patterns). Such 2-D data set can be obtained by taking sequential measurements from a single ITP channel, or (preferably) by taking parallel measurements from several ITP channels simultaneously. For example, as shown on FIG. 1d, an ITP arrangement can have several different LE wells (LE1, LE2, and LE3) that all connect to the same TE well (TE) via parallel channels. In this example, the channels have narrow regions 130 and wide regions 120 as described above. Any number of ITP channels can be used in parallel for such an approach.

BRIEF DESCRIPTION OF THE DRAWINGS

FIG. 2 shows experimental FCA assay results for analyte detection.

FIG. 3 shows experimental FCA assay results for analyte detection in cationic ITP.

DETAILED DESCRIPTION

Figure 1:
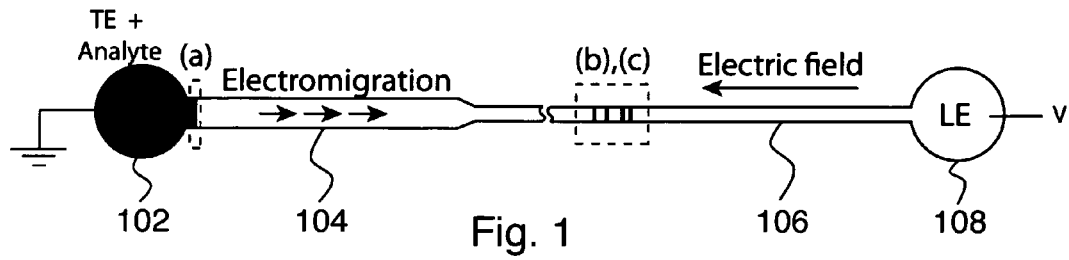
FIG. 1 shows an ITP configuration relating to embodiments of the invention.
Figure 1A:
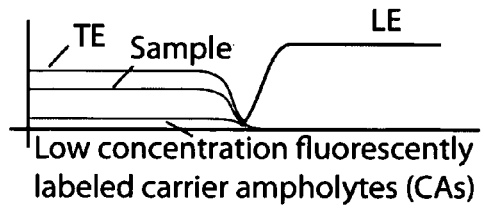
FIGS. 1a-c show enlarged schematic views of several locations shown on FIG. 1.
Figure 1B:
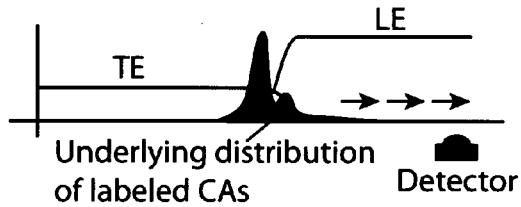
Figure 1C:
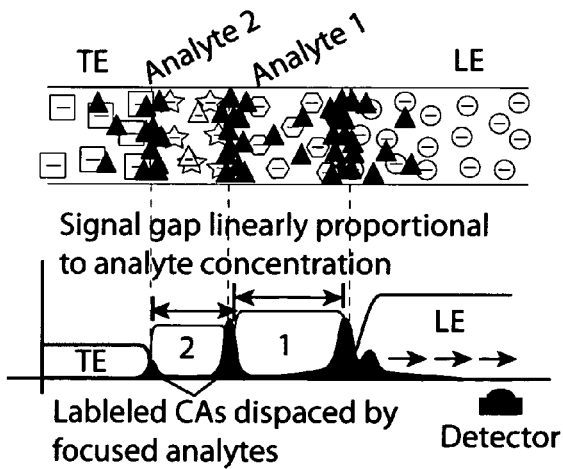
Figure 1D:
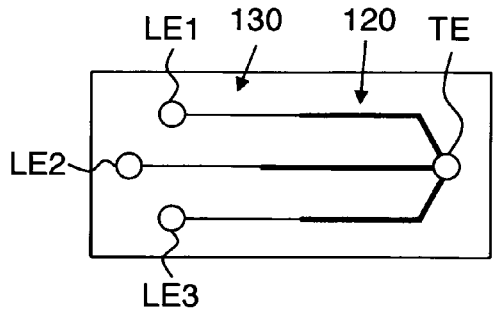
FIG. 1d shows an arrangement for performing FCA assays in parallel.

In section A below, experimental work relating to FCA analyte detection is described. Section B below relates to FCA identification of analytes.

A) Analyte Detection

We demonstrate a new fluorescence-based indirect detection technique which leverages ITP and a mixture of a large number (order 1,000) of fluorescently labeled carrier ampholytes (CAs) as mobility markers. We mix analytes with fluorescently labeled CAs and segregate and focus the mixture using ITP. Each analyte can be detected and quantified as one of many possible gaps in the fluorescent CA signal. In contrast to the mobility marker implementation of Khurana and Santiago (described in section A5 below), the current method does not require a priori choice of fluorophores and can be readily applied (without extensive and specific design) to a wide range of analytes. We discuss the principles of the method and demonstrate its use for the detection of several ideal analyte molecules. We present first experimental results using a microscope-based system; and we demonstrate the use of this technique for the detection of 2-nitrophenol (2NP) and 2,4,6-trichlorphenol (TCP) in tap water, without prior preparation steps. These are products and intermediates of industrial processes (e.g., production of plastics, drugs, herbicides) and common water pollutants, and have been classified as priority pollutants by the US Environmental Protection Agency. We then demonstrate the detection of these toxins using our hand-held, USB powered electrophoresis device.

A1) Fluorescent Carrier Ampholytes Assay

Carrier ampholytes (CA) are mixtures of amphoteric species, typically artificially synthesized polypeptides. They are typically used in isoelectric focusing (IEF) to produce a stationary pH gradient. Commercially available CA contain between a few hundred to a few thousands (more exact estimates are typically proprietary information) different amphoteric species, which possess a range of isoelectric points (pI). In IEF, a channel or gel separation column is filled with an ampholyte mixture. Under an applied electric field, ampholytes electromigrate, focus, and self-segregate to their respective pI, resulting in (an approximately linear) pH gradient. Amphoteric analytes introduced into this mixture electromigrate through the established pH gradient, separate, and focus at locations corresponding to their respective pI values. High concentrations of (non-fluorescent) CAs have been previously used with ITP to create a range of spacers between directly detectable analytes.

These traditional applications of CAs are in sharp contrast to their use in the assay we propose here. In this work, we use a low concentration (order 1 µM or lower) of CAs to create a mixture of fluorescently labeled species with a large distribution of pKa values. By using these labeled CAs in an environment whose pH is set primarily by the LE buffer (as is typical in ITP), we obtain species with a large distribution of finite (non-zero) effective electrophoretic mobilities.

In contrast to IEF, ITP uses leading (LE) and trailing electrolytes (TE) to buffer and determine system pH with a relatively narrow range (often a pH difference of 1 pH unit or less between LE and TE). Under these conditions, a mixture of CAs introduced into the system can be regarded as a mixture of species with a large distribution of effective mobilities, determined by the relative difference between each pKa and local pH. Many available CAs contain one or more primary amine groups, which makes them suitable for labeling with amine reactive dyes. We use such labeling to create a large collection of fluorescent species with a wide range of closely spaced effective mobilities.

FIGS. 1 and 1a-c schematically show the principles of the technique. We fill a channel and one of the end-channel reservoirs 108 with LE. As we will discuss further below, the channel preferably includes two sections of different widths (i.e., 104 and 106) to improve assay sensitivity. We fill the other reservoir 102 with a mixture containing the TE, sample, and a low concentration of prelabeled CAs. The resulting initial condition is shown on FIG. 1a. In the absence of analyte ions, application of an electric field causes a subset of CAs to focus into a contiguous zone of fluorescence (the negative control shown on FIG. 1b) between the LE and TE. When analyte ions are mixed with the TE, they also focus between LE and TE and thereby displace groups of fluorescent CAs. Analyte zones are detectable indirectly as "gaps" in the fluorescent signal, as shown on FIG. 1c. For a fixed detection site, the gap width is proportional to initial analyte concentration. The use of a large number of labeled CAs as markers yields unprecedented resolution and dynamic range. Multiple analyte detection is accomplished via ITP separation physics with a single fluorescence emission wavelength.

The use of a large number of FCAs as markers implies that very little a priori knowledge of analyte ion mobility is required for a wide range of analytes. Analytes should focus between LE and TE and have an effective mobility also bracketed by the very large range of CA mobilities. The large number of FCAs also implies a high dynamic range of identifiable analyte mobilities. A fluorescence zone will appear between any two analyte zones, provided that some subgroup of CAs possesses effective mobilities bracketed by the two analytes. The main limitation of the technique is that it is unable to detect analytes whose effective mobilities are higher than those of all the CAs (e.g., in anionic ITP, strongly ionized acids can have relatively high mobility). For weak electrolyte analytes, it is typically possible to design the pH of the system (by specifying the LE buffer) to achieve an effective mobility within the range of FCA mobilities.

A2) Theory

For low analyte concentrations and short times, the analyte in FCA assay is in "peak mode" where it contributes negligibly to local conductivity. For increasing focused analyte concentrations, the analyte contributes more significantly to the local conductivity and eventually displaces CAs, effecting a noticeable change in the fluorescent signal. The limit of detection (LoD) of our assay can be described as the minimum analyte concentration for which a local decrease in the baseline CA signal can be detected (versus noise and run-to-run variations). In practice, minimizing the LoD is equivalent to maximizing the width of the plateau-mode analyte zone width for a given initial analyte concentration.

In this section, we consider on-chip FCA ITP with semi-infinite sample injection (sample is mixed in the TE reservoir) and discuss the effects of the microchannel geometry on the length (and therefore LoD) of analysis zones, and its effect on the total analysis time. Details on the fabrication of a single channel with large cross-section variation are provided in section A32 below.

For simplicity, we here assume fully ionized species and a constant driving current; but the scaling derived adds significant intuition to more general cases. Consider a channel as in FIG. 1 which includes two sections: a loading section 104 with a large cross section area where the analyte is focused initially, and a detection section 106 with a small cross section area where the analyte is detected. The rate of accumulation of a species A in the loading section is given by its flux into the ITP interface, $$\dot{N}_t = (E_{TE}\mu_A - V_{ITP})A_L c_A^0. \tag{1}$$

Here, $E_{TE}$ denotes the electric field in the TE region, $\mu_A$ is the electrophoretic mobility of the analyte, $V_{ITP}$ is the ITP velocity in the loading section, $A_L$ is the cross-section area of the loading section, and $c_A^0$ is the analyte concentration in the adjusted TE zone. The relation between $c_A^0$ and the concentration of the analyte in the reservoir is given in the literature. In the adjusted TE region (where ion concentrations are locally uniform so that contributions of diffusive flux to ionic current are negligible) we can write the relation between the electric field, current I, cross section area A, and the conductivity $\sigma$ as $E=I/(A\sigma)$. Combining this with the ITP condition that $V_{ITP}=E_{TE}\mu_{TE}=E_{LE}\mu_{LE}$ and substituting the relations into Eq. 1 yields $$\dot{N}_t = \left(\frac{\mu_A}{\mu_{TE}} - 1\right)\frac{\mu_{LE}}{\sigma_{LE}} c_A^0 I, \tag{2}$$

where the subscripts LE and TE respectively denote properties of the leading and trailing electrolytes. Assuming negligible EOF, the temporal rate is related to the spatial (local, Eulerian) rate by $\dot{N}_x = \dot{N}_t/V_{ITP}$, yielding the relation $$\dot{N}_x = \left(\frac{\mu_A}{\mu_{TE}} - 1\right) A_L c_A^0. \quad (3)$$

Here $\dot{N}_x$ represents the number of ions accumulated per distance traveled by the ITP interface, and has units of mol/m. Using the subscript CI to denote a property of the counterions, the plateau concentration of the analyte is then given by:

$$c_A^P = c_{LE} \frac{\mu_A}{\mu_{LE}} \frac{\mu_{LE} - \mu_{CI}}{\mu_A - \mu_{CI}}. \quad (4)$$

Next, we will assume the accumulation of analyte in the detection section is negligible compared to its accumulation in the loading zone. This is reasonable for loading-to-detection section area ratios of a few fold or greater since, as shown by Eq. 3, the accumulation amount scales with the local channel area. Under this assumption, the total number of analyte moles accumulated is simply $N = \dot{N}_x L_L$, where $L_L$ is the length of the loading section. The length of the analyte zone in the detection section is then given by $L_A = N/(c_A^P A_D)$, where $A_D$ is the cross section area of the detection section. Combining this with Eqs. 3 and 4 yields an explicit, approximate expression for the length of the analyte zone, $$L_A = \frac{\mu_{LE}}{\mu_{TE}} \frac{(\mu_A - \mu_{TE})(\mu_A - \mu_{CI})}{\mu_A(\mu_{LE} - \mu_{CI})} \frac{c_A^0}{c_{LE}} \frac{A_L}{A_D} L_L. \quad (5)$$

The signal-to-noise ratio (SNR) associated with the detection of an analyte can be defined as $SNR_A = L_A/\delta$, where $\delta$ is the average width of fluorescent regions dispersing into each side of the analyte zone. A high $SNR_A$ indicates an analyte zone that is long compared to the characteristic width of these adjoining fluorescent regions. An exact expression for the width $\delta$ is not available, as it depends on both the mobilities of its neighboring analyte and the mobilities of the focused CAs, which are not known a priori. However, an analytical expression for this characteristic diffusion-limited focusing length given in the art shows that $\delta$ is inversely proportional to the current density. Hence, at the detector site we can expect $\delta \propto A_D/I$. Furthermore, because of the low currents used in ITP, power sources (in particular those of portable devices) are typically voltage limited (and not current limited). Assuming the resistance of the (large cross section) loading section is negligible, the maximum obtainable current is $I_{max} = V_{max} \sigma_{TE} A_D/L_D$. Substituting the latter expressions into Eq. 5 and our definition of $SNR_A$, we have $$SNR_A \propto V_{max} \frac{A_L}{A_D} \frac{L_L}{L_D} c_A^0. \quad (6)$$

This result shows that the analyte SNR (and hence the LoD of the assay) is proportional to the ratios of cross sections between the loading section and the detection section, as well as to the ratio of their lengths. Importantly, these geometrical parameters also affect the analysis time. The ITP velocity is inversely proportional to the cross section area. Therefore, for a large cross-section area ratio, the time for an analyte zone to travel through the detection region can be neglected compared to the time in the loading section. Hence, the total assay time can be approximated by the length of the loading section divided by the local ITP velocity, $L_L/V_{ITP}$. Using the expression for the maximum current, we obtain $$t_{detect} \propto \frac{1}{V_{max}} \frac{A_L}{A_D} L_L L_D. \quad (7)$$

Thus, the larger the cross-section area ratio and the larger the length of the channel section, the longer the analysis time. Clearly, there is a trade-off between the analyte SNR (and LoD) and analysis time. Optimization of the channel geometry according to these principles is within the skill of an ordinary art worker. As described in section A32 below, we used this result to design a microfluidic chip with a cross-section area ratio of 17 in order to compensate for the limited voltage available in our hand-held device (200 V), while maintaining a reasonable analysis time of approximately 10 min.

A3) Experimental Section
A31) Carrier Ampholytes Tagging

We used two mixtures of carrier ampholyte with different isoelectric point ranges, ZOOM® 3-10 and ZOOM® 9-11, both obtained from Invitrogen (Carlsbad, Calif.). Each of the mixtures was individually labeled with an amine reactive dye, Alexa Fluor 647 carboxylic acid succinimidyl ester, also from Invitrogen (catalog number A-20006).

The CAs labeling protocol we developed is adapted from the protein labeling protocol provided by Invitrogen. We mixed 1 mg of Alexa Fluor 647 in 100 µl of DMSO, and stored it in 10 µl aliquots at −20° C. We prepared a stock solution of 0.2 M sodium bicarbonate (pH 8.3) obtained from J. T. Baker (Phillipsburgh, N.J.). We prepared a stock solution of CAs by mixing 25 µl of ZOOM® (originally 40% in aqueous solution) in 1 ml of 0.2 M sodium carbonate. This mixture was kept refrigerated at 4° C. Finally, we prepared a stock solution of labeled CA by mixing 10 µl of ZOOM® in NaHCO$_3$ with 10 µl of Alexa Fluor 647. We centrifuged the mixture for approximately 10 seconds and incubated it at room temperature for 1 h. Assuming an average molecular weight of ~500 Daltons for the CAs, their final labeled concentration is about 10 mM. The specifications below for labeled CAs concentrations are with respect to this estimated concentration (e.g. 1 µM labeled CAs is a 10,000× dilution of this stock solution).

A32) Materials and Instrumentation

For all anionic ITP experiments the LE was composed of 10 mM lactic acid and 20 mM bis-tris (pH 6.4) in deionized water (UltraPure DNase/RNase free distilled water, GIBCO®Invitrogen, Carlsbad, Calif.). The TE was composed of 10 mM tricine and 20 mM bis-tris (pH 7.4) in all experiments, but the concentration of analytes and labeled CAs (which were mixed with the TE buffer), as well as the purity of the sample water (distilled vs. tap water) varied between experiments and are provided below. To both the LE and TE we added 1%~1 MDa poly(vinylpyrrolidone) (PVP) for suppression of electroosmotic flow (EOF).

For the experiments demonstrating the principle of the technique (results of FIG. 2), we used MES, ACES and BES as ideal analytes and mixed them in the TE together with 1 µM of labeled CAs. We diluted these analytes to their final concentration from 1 M stock solutions. This TE/sample mixture was based purely on deionized water. For the experiments demonstrating the detection of toxic chemicals, we prepared stock solutions of 1 mM 2,4,6-trichlorophoneol and 10 mM 2-nitrophenol. These analytes were diluted into a TE/sample mixture which had a final composition of 50% deionized water and 50% tap water. The tap water used was from a single stock solution obtained from the city water supply at Stanford University (Stanford, Calif.) on May 19, 2008, with no additional preparation steps. All buffers and analytes were obtained from Sigma Aldrich (St. Louis, Mo.).

We performed control and calibration experiments (and imaging) using a standard benchtop microscope or alternatively using a portable device. We first describe the former which was an inverted epifluorescent microscope (IX70, Olympus, Hauppauge, N.Y.) equipped with a 100 W mercury bulb (Ushio Inc., Tokyo, Japan), XF100-2 filter-cube from Omega Optical (Brattleboro, Vt.), a 10× (NA=0.3) UPlan-Flobjective and a 0.63× nonparfocalizing adapter. Images were captured using a 12 bit, 1300×1030 pixel array CCD camera (Micromax1300, Princeton Instruments, Trenton N.J.). We controlled the camera using Winview32 (Princeton Instruments, Trenton N.J.) and processed the images with MATLAB® (R2007b, Mathworks, Natick, Mass.). We applied voltage using a high-voltage sourcemeter (model 2410, Keithley Instruments, Cleveland, Ohio). For the experiments performed on the microscope, we used off-the-shelf microfluidic borosilicate chips (model NS-95) from Caliper Life Sciences (Mountain View, Calif.). The channel is isotropically etched with a depth of 12 μm and consists of a 54 μm wide section which constricts into a 34 μm wide section. The total length of the channel is 34.6 mm, with the initial (wide) section 11.5 mm in length. All data shown here were captured in the narrow region of the channel at a distance of 18.5 mm from the TE reservoir, 7 mm from the constriction.

Figure 6:
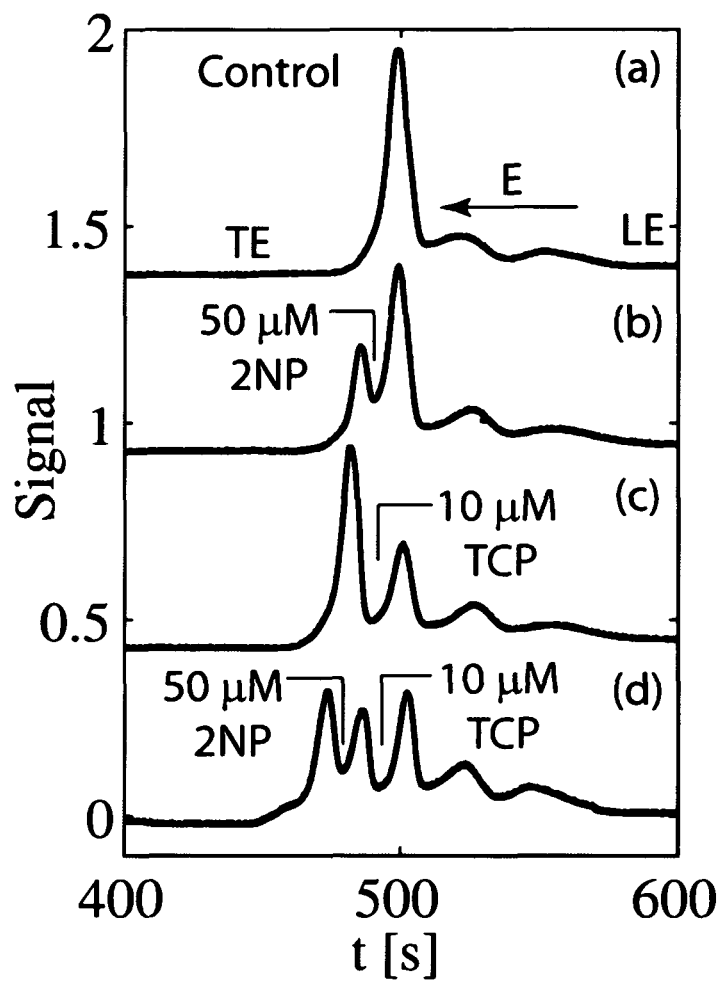
FIG. 6 shows FCA results from a hand held FCA instrument.

For the data of FIG. 6, we applied the FCA technique to the detection of 2NP and TCP in our portable device. This device is a hand-held electrophoresis instrument with laser induced fluorescence detection, which includes a microfluidic chip, high voltage generation, switching, illumination, detection, and central processing. It is powered and controlled via USB connected to a notebook computer. This portable device has a metal casing which acts as a Faraday cage to reduce environment noise. Central to the hand-held device is a single microelectronic chip (total silicon area of ~4 mm×4.5 mm and power consumption of 28 mW). In its current implementation, the device is capable of sourcing up to 200 V. The experiments on the device were performed using custom borofloat microfluidic chips we designed and built. The chip dimensions are 1.5×2.0 cm, and similar to the Caliper chip, it has a variable cross section area. However, instead of varying the mask width we used a two etch mask process wherein we varied the etch time of the two channel segments. The large cross-section is 55 μm wide, 25 μm deep and 11 mm long. The small cross section is 15 μm wide, 5 μm deep and 17 mm long. The variable etching time affects both the width and the depth of the channel and results in a 17× cross section ratio, vs. a 2.4× ratio in the Caliper chip. The detector was located at a distance of 20 mm from the TE reservoir (9 mm from the channel constriction).

A4) Results And Discussion

A41) Principles and Demonstration of the Technique Using a Standard Microscope

FIG. 2 shows calibration and control experiments for the FCA technique. We here use several (well known, well characterized) Good's buffers as idealized analytes. More specifically: (a) The control case shows the distribution of fluorescent CAs in the "ultra pure" water sample. (b) 10 μM of MES is mixed with the TE, and creates a zone between the LE and TE. The zone displaces labeled CAs resulting in a new gap in the signal. (c), (d) 10 μM each of ACES and BES are sequentially added, further displacing the labeled CAs and resulting in additional gaps in the signal. All signals and images are normalized by their maximum value. LE is 10 mM Lactic acid, TE is 10 mM tricine and counterion is 20 mM bis-tris. 1 μM of ZOOM® 3-10 labeled with Alexa Fluor 647 was mixed in the TE. ITP was performed at a constant current of 0.2 μA, with a 100 ms exposure time. The time elapsed from initiation of the voltage to arrival of the analytes to the detector is approximately 120 s.

In the negative control (FIG. 2a) no analytes are present and a large subset of the labeled CAs with effective mobilities between those of the LE and TE focus at the interface. We hypothesize that the underlying distribution of the CA signal (which resembles several large, overlapping peaks) is affected by buffer impurities. Nevertheless, these impurities and the CAs form a standard baseline signal associated with this CA mixture in the absence of analytes of interest. In FIG. 2b, we show the effect of adding 10 μM of MES to the TE mixture. A new plateau ITP zone is created by MES, displacing a subset of the CAs. The displacement results in a new gap in the fluorescence signal (whose width is directly proportional to its initial concentration. In other words, analytes with respectively higher and lower effective mobilities are displaced by the analyte toward the LE and TE.

In FIG. 2c, we show the effect of a second analyte, ACES, mixed with the TE. The ACES zone causes a new gap in the signal. The intensity of the fluorescent peak trailing the MES zone has decreased, as part of the CAs were displaced to a new location (trailing the ACES zone). FIG. 2d shows similar displacement with the addition of BES. Note the reproducibility of the signal shape away from analyte zones. For example, note the width and relative location of the peaks to the right of the MES in all four experiments. Signal analysis and interpretation of the results benefit from this repeatability.

The data of FIG. 2d shows that the number of CAs with mobilities lower than BES (to the left in the figure) is small compared to the total number of CA. This results in a low-area local peak on the trailing end of the CA signal, and suggests that the carrier CA mixture used here (ZOOM® 3-10) has fewer species with pKa values sufficiently high to yield effective mobilities low relative to BES. Below we will discuss the redistribution of CA signals by use of CAs of mixtures designed for a different pH range.

As described in section B below, an integral curve of CA fluorescence intensity can be used to extract information about the effective mobilities of the analytes, thus assisting in identification. Integration of the signal may also help make the analysis more robust to noise. Here we focus on other properties of the technique and its implementation on a hand-held device.

FIG. 3 presents a similar detection sequence for cationic ITP, where the CAs are labeled with carboxyrhodamine 6G. The LE is 1 mM sodium hydroxide and 20 mM HEPES. The TE is 10 mM Pyridine and 2 mM HEPES.

A42) Detection of 2,4,6-Trichlorophenol (TCP) in Tap Water Using a Microscope

Figure 4:
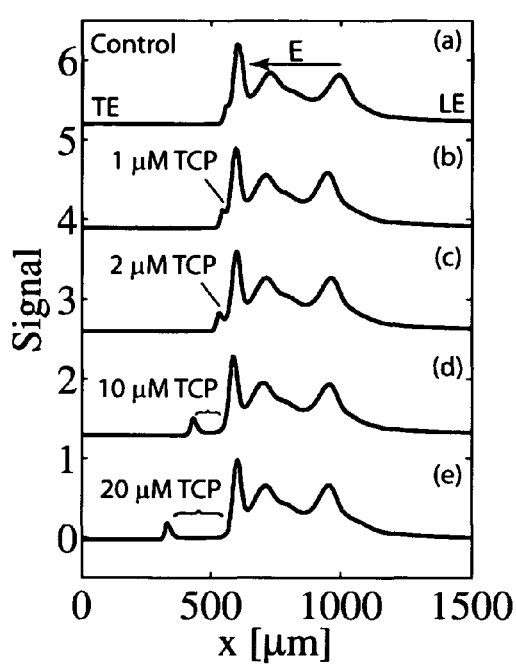
FIG. 4 shows the effect of increasing analyte concentration in an FCA assay.

FIG. 4 presents quantitative detection of TCP in tap water, without additional sample preparation steps. More specifically: (a) In the control, we observe the underlying distribution of labeled CAs which are likely affected by impurities inherent in the water sample. We consider this as the baseline signal. (b-e) When TCP is added at a range of concentrations from 10 to 100 μM we see the formation of a signal gap with SNR proportional to initial analyte concentration. Buffers, labeled CAs, microchannel geometry, and applied current are the same as in FIG. 2.

We spiked tap water with a range of TCP concentrations and mixed it with the TE and labeled CAs, resulting in a 2× fold dilution of the sample. We then applied ITP directly to that sample. As in the previous example, subsets of labeled CAs are displaced by and bracket the TCP zone. The width of the gap in the signal (analyte zone width) is proportional to the initial concentration of the analyte, as per Eq. 5. The LoD is reached when the local minimum of the signal can no longer be resolved relative to normal, local fluctuations. FIG. 4b shows the minimum concentration for which a new minima in the signal is first discernible with confidence. We note that in these experiments we focused on illustrating the applicability of the technique to relevant water pollutants. As discussed in the theory section, the LoD of the technique is strongly dependent on the channel geometry and buffer chemistry. Here we used a commercial chip and a high concentration TE buffer, two controlling variables which could be significantly improved to achieve lower LoD. We estimate the current LoD of the FCA technique is approximately 1 $\mu M$ for most analytes (e.g., see data of FIG. 4). It is expected that this LoD can be further improved.

A43) Redistribution of CA Signal and Detection of Multiple Toxins in Tap Water

The FCA technique allows for detection of multiple analytes present in the sample. In this section, we apply the technique for the detection of 2NP and TCP in tap water. We also use this example to illustrate how the associated distribution of CAs relative to analytes can be modified to change the range of detectable analyte mobility and SNR.

Figure 5:
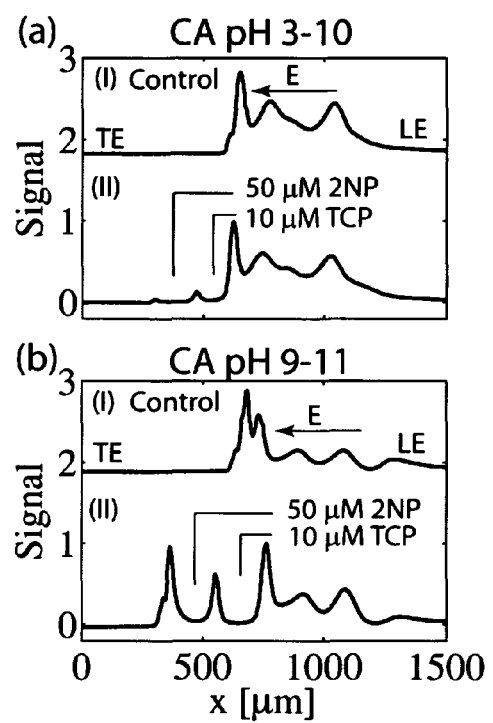
FIG. 5 shows the effect of altering the CA pH range in an FCA experiment.

FIG. 5 shows detection of 2-nitrophenol (2NP) and 2,4,6-trichlorophenol (TCP) in tap water (in a microscope) using (a) CAs with a pI range of 3-10, and (b) CAs with a pI range of 9-11. For both cases: (I) The control (no analytes) shows several peaks, corresponding to impurities in the tap water; and in (II) 50 $\mu M$ of NP and 10 $\mu M$ of TCP are introduced in the TE reservoir. Each displaces a subset of fluorescent CAs resulting in new gaps in the signal. At the working pH (~6.4 in the LE, ~7.4 in the TE), the pI 9-11 CA mixture provides a larger number of low (effective) mobility CAs and thus contribute to the area and magnitude of the peaks bracketing the analytes. Experiments were performed on an epifluorescent microscope. LE and TE are the same as in FIG. 2. We here used 1100 V applied voltage with 2 ms exposure. The time elapsed from initiation of the voltage to arrival of the analytes to the detector is ~60 s.

FIG. 5 presents an experiment where 2NP and TCP are both detected in tap water. We first note the underlying baseline of the CAs, which resembled several overlapping peaks. In these experiments we used labeled CAs with a pI range of 3-10 (the broadest range commercially available from most vendors). While the CA zones bracketing TCP and 2NP are clearly visible, the area under the curve of CAs which are on the TE side of the 2NP zone is low (reflecting a low number of CAs with effective mobilities lower than 2NP).

One possible approach to improve the signal in the case above is to choose a counter-ion with a higher pKa, thus increasing the pH of the entire system and increasing the effective mobilities of the two analytes. Depending on the (unknown) pKa values of the CAs this may result in the analytes displacing a larger number of CAs and increasing the signal. However, this approach carries the inherent disadvantage that increasing the pH of the system also increases the effective mobility of the TE. Since the focusing rate is proportional to the ratio of analyte to TE mobilities (Eq. 3), this will lead to shorter analyte zones and will adversely impact the limit of detection. An alternative approach is to use a different CAs mixture which, for a given pH, is expected to include a larger number of low effective mobility CAs. CAs with higher isoelectric points are also expected to have higher pKa values and therefore lower (anionic) effective mobilities.

In FIG. 5b we present a second experiment, identical to that of FIG. 5a, except we here use labeled CAs with a pI range of 9-11 (highest range commercially available). As expected, these CAs have lower effective mobilities and a larger fraction of them focus between the analytes and the TE. This results in more confidence associated with the identification of the signal gap (e.g., here the signal to noise ratio of the peak of slower CAs is approximately 20 fold higher than in FIG. 5a). This enrichment process in which the fluorescence intensity of signal peaks can be re-distributed is especially important for implementation on miniaturized and low-cost devices where often the dynamic range and sensitivity of the sensor may be low compared to benchtop, microscope-based systems.

A44) Implementation of the Fluorescent Carrier Ampholyte Assay for Toxins Detection in a Handheld Device Lastly, we integrate the analyses and experience associated with the theory and empirical, detailed imaging analysis to demonstrate the detection of unlabeled toxins (2NP and TCP) in untreated tap water in our portable device (c.f. Materials and Instrumentation above). FIG. 6 presents detection of unlabeled 2NP and TCP in tap water using the above-described hand-held ITP device. LE and TE composition are the same as in FIG. 2. 200 V was applied along a 23 mm channel with a 17:1 cross section area variation (the detection region is 17 mm long). Despite lower available voltage and longer analysis time, the handheld device successfully detects both toxins.

We used the same CAs (pI range of 9-11) as in FIG. 5b, but here we implemented the assay in our hand held device rather than a standard microscope system. The most significant differences between the hand-held device and the benchtop system are the lower spatial resolution of the detector, and the associated limit on high voltage (the hand-held device is currently limited to 200 V). Both limitations result in wider (more diffused) gradients in the CA signals (larger values of $\delta$ in Eq. 6) and therefore reduce the LoD. To provide some compensation for these limitations, we designed microfluidic channels with a high (17×) cross section area ratio. As shown by Eq. 5, higher area ratio implies proportionally longer analyte zones in the detection section. Furthermore, as the zone enters the detection section, current density increases 17-fold resulting in sharper ITP interfaces (smaller $\delta$ values). Both parameters contribute on an increase in the SNR associated with analyte detection (as per Eq. 6).

In FIG. 6 we show detection of 2NP and TCP at concentrations equal to those in the microscope based experiments presented earlier. Note some finer features of the signal have been lost to the lower resolution of the detector. Furthermore, as indicated by Eq. 7, while a large area ratio improves the resolution of the assay, it also increases the total analysis time. As indicated by the (temporal) isotachophorerogram, the total analysis time on the hand-held device was approximately 10 min. Clearly, there is a tradeoff between resolution and analysis time which is a strong function of maximum voltage, channel geometry (both length and area ratios), and buffer chemistry.

A5) Comparison with Other Analysis Approaches

Khurana and Santiago (US 2008/0197019 and Anal. Chem. 2008, 80, 279-286) presented an indirect detection ITP assay which uses mobility markers to identify and quantify unlabeled analytes. The approach mixes analytes with carefully selected fluorescent species (termed mobility markers) which focus into ITP zones along with analytes. Gaps in the fluorescence signal of the fluorescent markers then indicate the presence and quantity of the specific analytes which they bracket. The strong ion displacement physics of ITP resulted in the ability to detect ~10 uM non-fluorescent analytes while directly detecting order ~1 mM fluorescent markers Typically, analytes focus in peak mode (narrow, Gaussian-like shapes associated with low concentration) and so are easily identified using standard peak analysis. A disadvantage of the mobility markers technique is that marker molecules and ITP buffer conditions need to be specifically selected for each analyte; and there are typically only a limited number of available fluorophores with relevant mobilities. The present approach alleviates these disadvantages.

Fluorescently labeled CAs have been used in locating ITP interfaces in a gel, but not in free solution and not for the purpose of specifically identifying sample species by analyzing the fluorescent signal. Schafer-Nielsen et al. (Journal of Biochemical and Biophysical Methods, 3, 1980, 97-128) performed ITP of human serum proteins with standard (non-fluorescent) molecular spacers to improve resolution. They added to the mixture fluorescently labeled CAs which focused at the boundaries of these spacers, in locations where they also expected their macromolecules to focus. They therefore used labeled CAs to identify the (co-located) focusing sites of their analytes; and this made easier the process of cutting zones out of the gel for sample extraction. Fluorescamine-tagged CAs (they used Ampholine, LKB, Sweden) were visualized using UV illumination.

A6) Analyte Detection Conclusions

We have developed a novel indirect-detection technique which allows detection of analytes with little a priori knowledge of their electrophoretic mobilities. The technique is based on the displacement of fluorescently labeled carrier ampholytes by focused analytes in ITP. The gaps in the resulting fluorescence signal are used to detect indirectly the analytes. We have demonstrated the detection of ideal analytes and of 2-nitrophenol and 2,4,6-trichlorophenol in tap water, without the need for labeling or sample preparation. We presented experimental demonstrations using both a standard microscopy based system and a hand-held device. The signal produced by the FCA assay can be easily detected using the highly simplified optics on our hand-held device. This opens the possibility for portable and low-cost detection systems for toxins in the environment.

Our current LoD is approximately 1 μM for most addressable analytes. This level of sensitivity is relevant for some pollutants such as 2-chlorophenol, 2,4-dichlorophenol and 2,4-dimethylphenol which are permitted by EPA at roughly 1 μM levels. However, further improvements are required to achieve order 10 nM for better limits of detection, necessary to meet EPA standards of other toxins such as 2-nitrophenol and 2,4,6-trichlorophenol. We believe that such sensitivity is possible with the current technique and so it can eventually become competitive with the sensitivity of high quality, existing (bench top) chromatography techniques.

We are currently exploring several directions to achieve this. First, we hypothesize that significant improvements in LoD are possible by optimizing the microchip geometry, particularly in increasing the cross-section area ratio. On the microscope system, a 50× ratio (vs. 2.4× in the off-the-shelf chip) should theoretically allow for ~50 nM detection. On the hand-held device, chip geometry optimization should be carried out in concert with efforts to increase system voltage to maintain suitably short analysis time. In addition, by applying an LE concentration cascade we believe an additional 10× increase in sensitivity is possible. Optimization of TE chemistry should also help. For example, reducing TE concentration and TE mobility (e.g., by choosing a TE with a higher pKa) would proportionally increase the focusing rate. We believe an additional factor of ~10 or more is possible with these improvements. Other possibilities for improved LoD include off-chip sample treatments for sample purification (as is often used with other systems).

In section B below, we present a signal analysis technique which enables analyte identification based on the fluorescent signal. As we have shown here, the higher the effective mobility of the analyte, the larger fraction of labeled CAs it displaces. Quantifying this fraction can be used to measure an analyte's effective mobility. Measurements of effective mobility at different pH conditions allows to extract the pKa and fully ionized mobility of the analyte, which assist in identification.

B) Analyte Identification

In this section we demonstrate how signals from the above-described FCA assay can be analyzed to achieve quantitative identification of analyte ions given little or no a priori knowledge regarding their physicochemical properties. We found that the amount of displaced fluorescent CAs can be directly related to the effective mobility of the unlabeled (non-fluorescent) analyte that displaced them. By constructing a calibration curve for this property, we are able to obtain quantitative measurements of the effective mobilities of analytes. We can obtain an estimate of the effective mobility of analytes using two LE buffers. We then combine these measurements with ITP theory to compute estimates of the dissociation constant and fully ionized mobility of analytes. This analysis method is tailored for the FCA assay, and enables rapid (~order 3 min) identification of unlabeled analytes.

We here illustrate the identification technique by applying it to two chemical pollutants: 2-nitrophenol (2NP) and 2,4,6-trichlorophenol (TCP), with no sample preparation steps. We begin by describing several principles and definitions and then show how to construct the calibration curves. We then use these curves to extract effective mobilities of detected species. Lastly, we describe how to obtain acid dissociation constants (pKa) and fully ionized mobility values from those effective mobilities.

B1) Principles And Definitions

Figure 7:
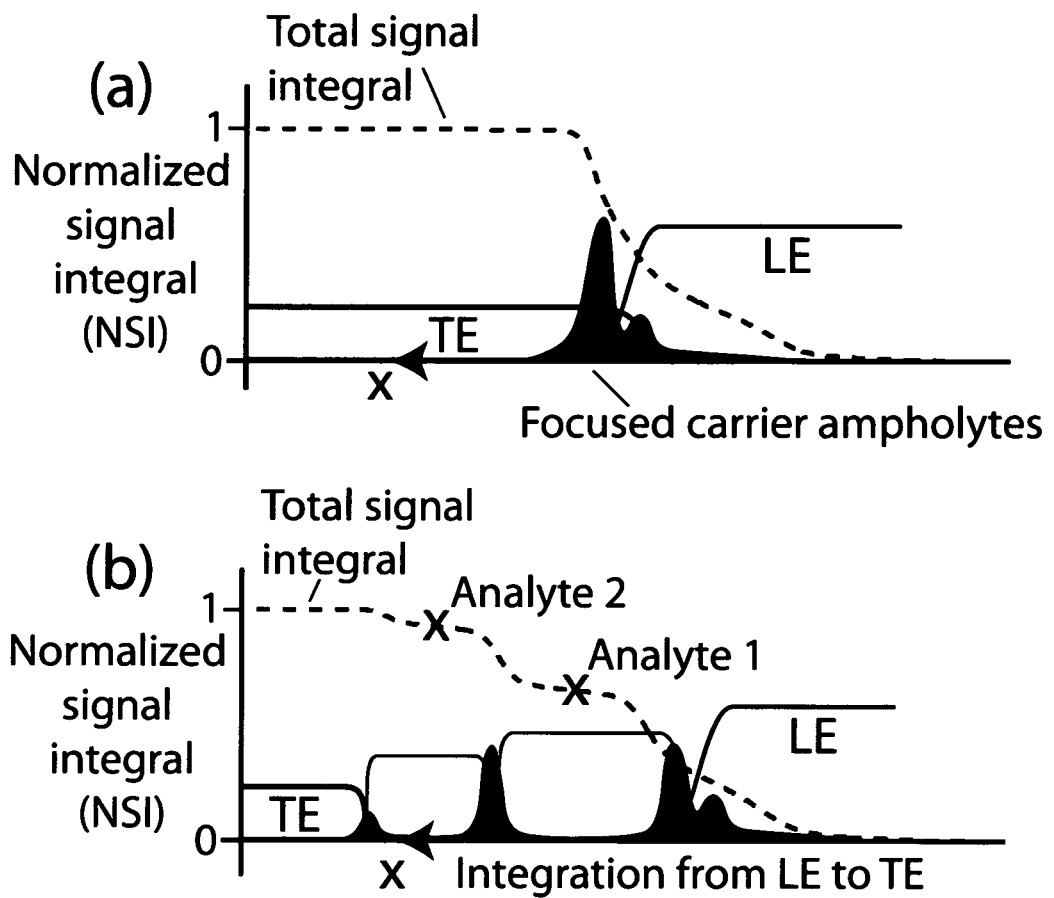
FIGS. 7a-b show the normalized signal integral (NSI) of an FCA assay.

FIG. 7 presents a schematic of the FCA assay. More specifically: (a) In the absence of analytes, labeled CAs focus at the LE-TE interface creating a continuous fluorescence signal. (b) Analytes focused under isotachophoresis displace subsets of the labeled CAs creating gaps in the signal. The normalized signal integral (NSI) (dashed curves) is a cumulative integral of the fluorescence signal from LE to TE. Plateau regions in the NSI (marked by X) are associated with gaps in the fluorescent signal and the presence of specific focused analytes. NSI values for each analyte are a measure of the fraction of CA between the analyte and the LE. The latter fraction can be related to the effective analyte mobility.

We define an axial coordinate, x, pointing from LE to TE. In the control ITP run (FIG. 7a), labeled carrier ampholytes are focused between the TE and TE creating a continuous (albeit non-uniform) fluorescence signal. The dashed line in FIG. 7a shows the cumulative integral of the fluorescent signal along x. The initial value of the integral is set to zero in the LE region where no labeled CAs are present. The integral increases monotonically until reaching a constant at the TE (where again no labeled CAs are present). For a given CA mixture and LE and TE buffer combination, this total signal integral is fixed and represents the cumulative intensity of all labeled CAs which focus at these conditions. We then define the quantity NSI (for "normalized signal integral") as the local integral value divided by the total integral, $$NSI(x) = \int_{x_{LE}}^{x} [I(x) - I(x_{LE})]dx \Big/ \int_{x_{LE}}^{x_{TE}} [I(x) - I(x_{LE})]dx, \quad (8)$$

where I is the fluorescence signal (averaged across the channel width), and $x_{LE}$ and $x_{TE}$ are axial coordinates in the LE and TE zones respectively. When I is obtained using a point detector, the coordinate x should be replaced with the time coordinate t. In the latter case, the definition of NSI makes it independent of the intensity of illumination, exposure time, or background signal. However, data obtained from 2D images (as in this work) has to be first corrected for non-uniform illumination and background.

As shown in FIG. 7b, analyte ions which focus between the LE and TE displace subsets of CAs, and thus create gaps in the fluorescence signal. While the total signal integral remains unchanged (fixed total amount of CAs), the shape of the NSI function changes and now includes a new region of locally nearly constant value of NSI. This plateau corresponds to an analyte zone (where few CAs are present). The location of this analyte-specific plateau in the NSI signal is determined by the analyte's effective mobility. A species with a higher effective mobility results in a larger fraction of CAs being displaced, and an associated lower NSI value for its plateau. If the exact content of the CA mixture were known (mobility and pKa values of all species), one would be able to derive an analytical relation between the effective mobility of an analyte and its corresponding NSI. However, since the exact content of CA mixtures is unknown (typically this is regarded as proprietary information by CA suppliers), we construct empirical calibration curves as described in the following sections.

B2) Experimental Section

B21) Carrier Ampholytes Tagging

We used ZOOM® 9-11 carrier ampholyte obtained from Invitrogen (Carlsbad, Calif.) and labeled them with Alexa Fluor 647, also from Invitrogen. The labeling protocol is similar to the one suggested by Invitrogen for labeling of proteins.

B22) Materials and Instrumentation

We used two LE buffers in the experiments. $LE_1$ was composed of 10 mM lactic acid and 20 mM bistris (pH 6.4) in deionized water (UltraPure DNase/RNase free distilled water, GIBCO® Invitrogen, Carlsbad, Calif.). $LE_2$ was identical to $LE_1$, with the addition of 4 mM sodium-hydroxide (pH 6.8). The TE was composed of 10 mM tricine and 20 mM bistris in all experiments, but the concentration of analytes and labeled CAs (which were mixed with the TE buffer) varied between experiments as described below. To both the LE and TE we added 1%~1 MDa poly(vinylpyrrolidone) (PVP) for suppression of electroosmotic flow (EOF).

We construct calibration curves (FIG. 9) using known concentrations of very well characterized weak electrolytes. For this purpose, we used 20 µM 2-(N-morpholino)ethanesulfonic acid (MES), 30 µM N-(2-Acetamido)-2-aminoethanesulfonic acid (ACES), 40 µM 3-(N-morpholino)propanesulfonic acid (MOPS), and 50 µM 4-(2-hydroxyethyl)-1-piperazineethanesulfonic acid (HEPES) and mixed these in the TE together with 1 µM of labeled CAs (we performed limited additional experiments where we included individual additions of these to verify their identities). We diluted these ideal analytes to their final concentration from 1 M stock solutions. For the experiments demonstrating the identification of phenols, we prepared stock solutions of 1 mM 2,4,6-trichlorophenol and 10 mM 2-nitrophenol. All buffers and analytes were obtained from Sigma Aldrich (St. Louis, Mo.).

We performed the experiments using an inverted epifluorescent microscope (IX70, Olympus, Hauppauge, N.Y.) equipped with a 100 W mercury bulb (Ushio Inc., Tokyo, Japan), XF100-2 filter-cube from Omega Optical (Brattleboro, Vt.), a 10× (NA=0.3) UPlanFlobjective and a 0.63× non-parfocalizing adapter. Images were captured using a 12 bit, 1300×1030 pixel array CCD camera (Micromax1300, Princeton Instruments, Trenton N.J.). We controlled the camera using Winview32 (Princeton Instruments, Trenton N.J.) and processed the images with MATLAB® (R2007b, Mathworks, Natick, Mass.). We applied voltage using a high-voltage sourcemeter (model 2410, Keithley Instruments, Cleveland, Ohio). We used off-the-shelf microfluidic borosilicate chips (model NS-95) from Caliper Life Sciences (Mountain View, Calif.). The channel for this experiment is isotropically etched with a depth of 12 µm and has a 54 µm wide section which constricts into a 34 µm wide section. The total length of the channel is 34.6 mm, with the initial (wide) section 11.5 mm in length. All data shown here were captured in the narrow region of the channel at a distance of 18.5 mm from the TE reservoir, 7 mm from the constriction.

B3) Results and Discussion

B31) Construction of a Calibration Curve

We first present the technique for construction of calibration curves. These curves relate NSI values to effective mobility. In this example we use $LE_2$, and perform an FCA experiment to detect simultaneously the well characterized analytes listed earlier. A list of the analytes, their dissociation constants and fully ionized mobilities are provided in Table 1 below.

Figure 8:
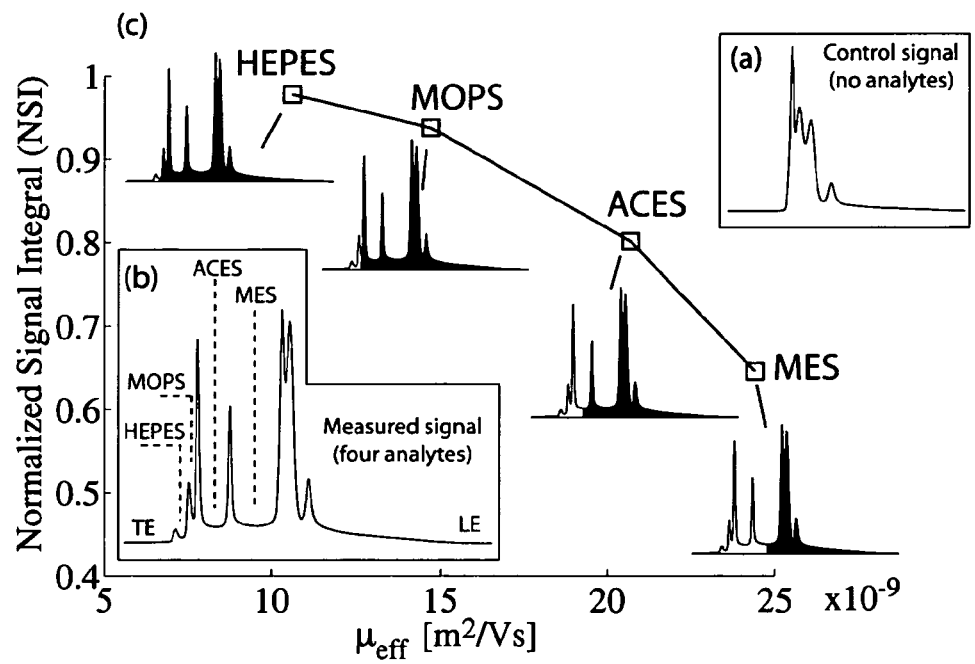
FIG. 8 shows construction of a calibration curve relating NSI to effective mobility in an FCA assay.

FIG. 8 shows construction of a calibration curve relating the value of NSI (area under the fluorescence signal) to the effective mobility of the analyte. (a) The control FCA signal in the absence of analytes (raw images of FCA signal shown with vertical dimension magnified 25 fold for clarity of presentation). (b) FCA signal for the case with four idealized, calibrant analytes (20 µM MES, 30 µM ACES, 40 µM MOPS, and 50 µM HEPES) with known electrophoretic mobility and pKa values. The assay was used for indirect detection of the analytes wherein groups of FCAs are displaced by the analytes, forming gaps (or 'valleys') in the fluorescent signal. (c) We calculate NSI values specific to each calibrant analyte using the integral of the FCA signal from LE to each analyte plateau. We plot this value versus the computed effective mobilities of the calibrants. This monotonic curve is used to extract the effective mobility of unknown analytes given measurements of their NSI.

TABLE 1

List of ionic species and their properties, as used in the calculation of effective mobilities appearing in the calibration.

| Species | Relevant valence | Fully ionized mobility [m²/Vs] | pKa |
| --- | --- | --- | --- |
| Lactic acid (LE) | −1 | 36.5E−9 | 3.86 |
| Tricine (TE) | −1 | 30.0E−9 | 8.1 |
| Bis-tris (counter ion) | +1 | 26.0E−9 | 6.4 |
| Sodium (counter ion) | +1 | 51.9E−9 | 13.7 |
| MES | −1 | 28.0E−9 | 6.1 |
| ACES | −1 | 31.3E−9 | 6.84 |

TABLE 1-continued

List of ionic species and their properties, as used in the calculation
of effective mobilities appearing in the calibration.

| Species | Relevant valence | Fully ionized mobility [m²/Vs] | pKa |
|---|---|---|---|
| MOPS | −1 | 26.9E−9 | 7.2 |
| HEPES | −1 | 23.5E−9 | 7.5 |

FIGS. 8*a* and 8*b* respectively present the control signal (in the absence of analytes) and the detection signal, showing four new gaps in the signal, corresponding to the focused analytes. Despite their relatively high concentrations, the MOPS and HEPES zones are significantly shorter than the MES and ACES zones. This is expected since the focusing rate of each analyte is proportional to the ratio of its effective mobility to the effective mobility of the TE. For a given pH, weak acids with higher pKa values have lower effective mobilities, accumulate at a lower rate, and result in shorter ITP zones.

We determine the value of the NSI for each analyte at the center of its respective plateau. The NSI can be interpreted as the area under the signal curve from the LE to the analyte. This is illustrated using the measured data (not schematics) in FIG. 8*c*, where the NSI value corresponds to the solid region under the curve. For this calibration case of known LE and known idealized analytes, we can compute analytically the effective mobilities of each of these analytes. With this information, we construct FIG. 8*c* which shows the monotonic curve relating analyte NSI value with its (here) known effective mobility.

Using this curve (and/or fits to this curve), NSI measurements of unknown analytes can be related to effective mobility values. The accuracy clearly depends on the resolution of the calibration curve. Lastly, we repeat this process and construct a second calibration curve for the same CAs and ideal analyzes but now using $LE_1$.

B32) Extraction of 2-Nitrophenol Effective Mobilities

Figure 9:
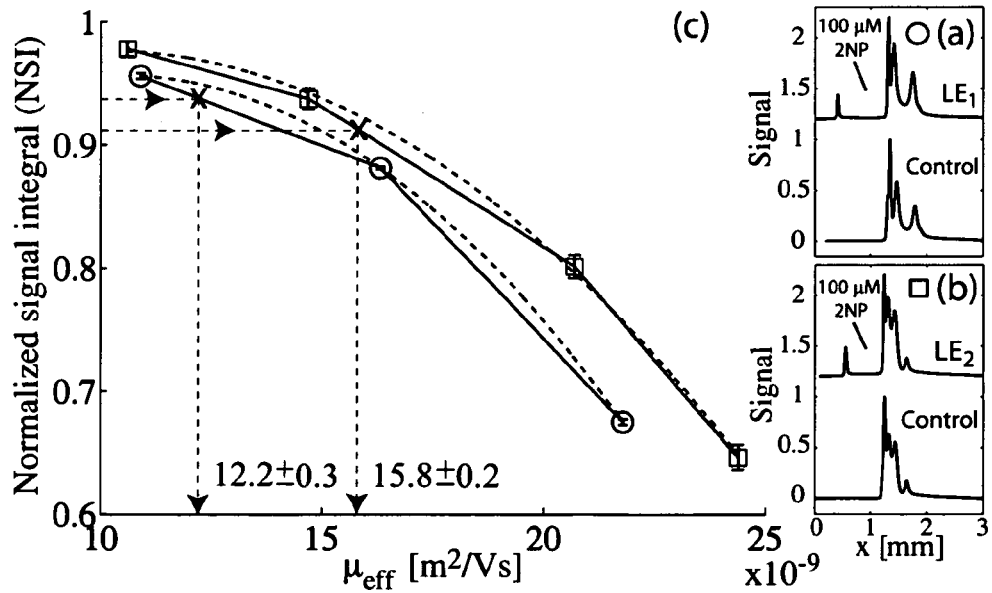
FIG. 9 shows extraction of effective mobility from NSI calibration curves.

FIG. 9 shows extraction of the effective mobility of 2-nitrophenol (2NP) at two pH values, from two NSI calibration curves. (a) Indirect detection of 100 μM 2NP using $LE_1$ (pH 6.4), (b) using $LE_2$ (pH 6.8). (c) We compute the NSI values of 2NP based on the two experiments, and present their values as horizontal dashed lines. At the points of intersection with the appropriate calibration curve, we draw vertical dashed lines which intersect the x-axis and indicate the measured effective mobility. Solid lines correspond to linear interpolation between the data point, and the dashed curves correspond to quadratic best-fits to each of the data sets. The uncertainty bars indicate 95% confidence on the mean given 3 repetitions.

FIGS. 9*a* and 9*b* present the indirect detection of 2-nitorphenol (2NP) using results from two different ITP buffer systems ($LE_1$ and $LE_2$). The two buffer systems are nearly identical, except that $LE_2$ contains an additional 4 mM of sodium hydroxide which servers as a source of counter-ion titrant and increases the pH through the ITP system. We used these experiments to compute NSI values of 2NP for the two buffers and obtained values of 0.94 and 0.91 respectively. FIG. 9*c* presents the calibration curves for both buffer systems (the curve for $LE_2$ is identical to the one presented in FIG. 8). We fitted the data points in the calibration curves using two approximations: a linear interpolation (solid lines) and a quadratic best fit (dashed curves). In the subsequent analysis steps we use both fitting approaches and compare their results.

We found the intersection of each NSI value with the respective curve (one intersection for each LE as shown by the horizontal dashed lines), and extracted the corresponding effective mobility estimates (vertical dashed lines). Using the linear interpolation approximation, we obtain for 2NP effective mobilities of $12.2(\pm 0.3) \cdot 10^{-9}$ and $15.8(\pm 0.2) \cdot 10^{-9}$ m²/Vs for $LE_1$ and $LE_2$, respectively. Using the quadratic best-fit we obtain respective mobilities of $13.4(\pm 0.3) \cdot 10^{-9}$ and $16.3(\pm 0.2) \cdot 10^{-9}$ m²/Vs.

B33) Calculation of pKa and Fully Ionized Mobility from Effective Mobilities

Given an LE buffer composition, the properties (e.g. concentration, effective mobility, conductivity) of any ITP plateau zone can be semi-analytically computed based on its fully ionized mobility and dissociation constants. Iterative inverse-problem algorithms which, given a set of effective mobility measurements, computes the fully ionized mobilities and dissociation constants of the analyte are known in the art. We here use the same approach, but provide a graphical representation of this inverse problem.

Figure 10:
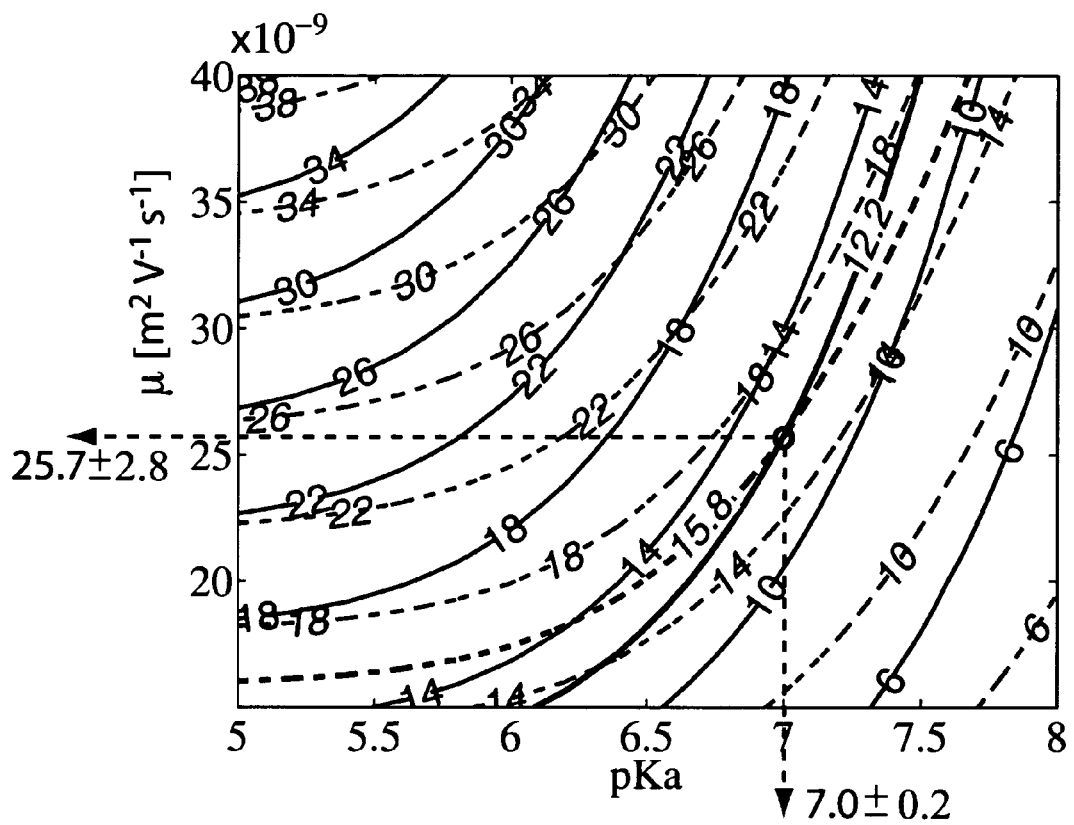
FIG. 10 shows extraction of fully ionized mobility and pKa from two effective mobility measurements at two different LE compositions.

FIG. 10 shows extraction of fully ionized mobility and pKa from two effective mobility measurements at two LE compositions. Two families of lines are presented, corresponding to two different LE compositions: $LE_1$ (pH 6.4, solid lines) and $LE_2$ (pH 6.8, dashed lines). Within each family, the contours represent the effective mobility of an analyte given the respective values of pKa and fully ionized mobility. The intersection of two effective mobility contour lines (one from each family) identifies the pKa and fully ionized mobility of a single species exhibiting these effective mobilities under the two chemistries. The thick lines indicate the effective mobility values obtained for 2NP from the fluorescent carrier ampholytes assay using the linear interpolation approximation for the calibration curves.

FIG. 10 assumes monovalent acids with pKa values ranging from 5 to 8, and fully ionized mobilities from $15 \cdot 10^{-9}$ to $40 \cdot 10^{-9}$ m²/Vs. For each mobility versus pKa combination (representing the properties of an individual analyte), we compute its effective mobility when in a pure ITP zone. This results in contours of effective mobility values in the field of pKa versus (fully ionized) mobility. This contour map is determined completely by the composition of the LE (e.g., does not depend on the CA or specific analytes of interest).

To obtain the fully ionized mobility and pKa given two effective mobilities, we look for the intersection point of the contour curves corresponding to those effective mobilities. For example, for 2NP using the linear interpolation approximation, we found the nominal effective mobility to be $12.2 \cdot 10^{-9}$ m²/Vs for the system with $LE_1$. This places the solution along the $12.2 \cdot 10^{-9}$ curve (marked as a thick solid line) of the $LE_1$ contour map. At the same time, the solution also lies on the $15.8 \cdot 10^{-9}$ curve (marked as a thick dashed line) of the $LE_2$ contour map. The solution must therefore lie at the intersection point, giving a pKa of $7.0(\pm 0.2)$ and a fully ionized mobility of $25.7(\pm 2.8) \cdot 10^{-9}$ m²/Vs. Similarly, using the quadratic best-fit approximation, we obtain a pKa of $6.7(\pm 0.2)$ and a fully ionized mobility of $22.3(\pm 23) \cdot 10^{-9}$. We know of no previous measurements of the mobility of 2NP, but its reported pKa value of 7.22 is in good agreement with our measurement of $7.0(\pm 0.2)$.

We performed the same process using 2,4,6-trichlorophenol (TCP) and obtained respective effective mobilities of $14.4\text{-}14.7 \cdot 10^{-9}$ and $16.2\text{-}16.8 \cdot 10^{-9}$ m²/Vs for $LE_1$ and $LE_2$, using the linear interpolation approximation. Using the quadratic approximation we obtained respective effective mobilities of $15.1\text{-}15.4 \cdot 10^{-9}$ and $16.8\text{-}17.4 \cdot 10^{-9}$. Here the ranges indicate the values given two repetitions of each experiment. Using the average of these values, FIG. 10 yields a pKa of 6.26 and a fully ionized mobility of $19.4 \cdot 10^{-9}$ m²/Vs (not shown in the figure) using the linear interpolation approximation, and a pKa of 6.1 and fully ionized mobility of $19.5 \cdot 10^{-9}$ using the quadratic approximation. Reported values for the pKa TCP range from 6.0 to 6.23, again in fairly good agreement with our measurement. We note that as demonstrated by the calibration curves, multiplexed detection and identification of analytes is also possible. In one experiment we could detect and identify 2NP and TCP simultaneously in the same ITP separation.

B4) Indirect Detection of Explosives and Endocrine Disruptor in River Water

Figure 11:
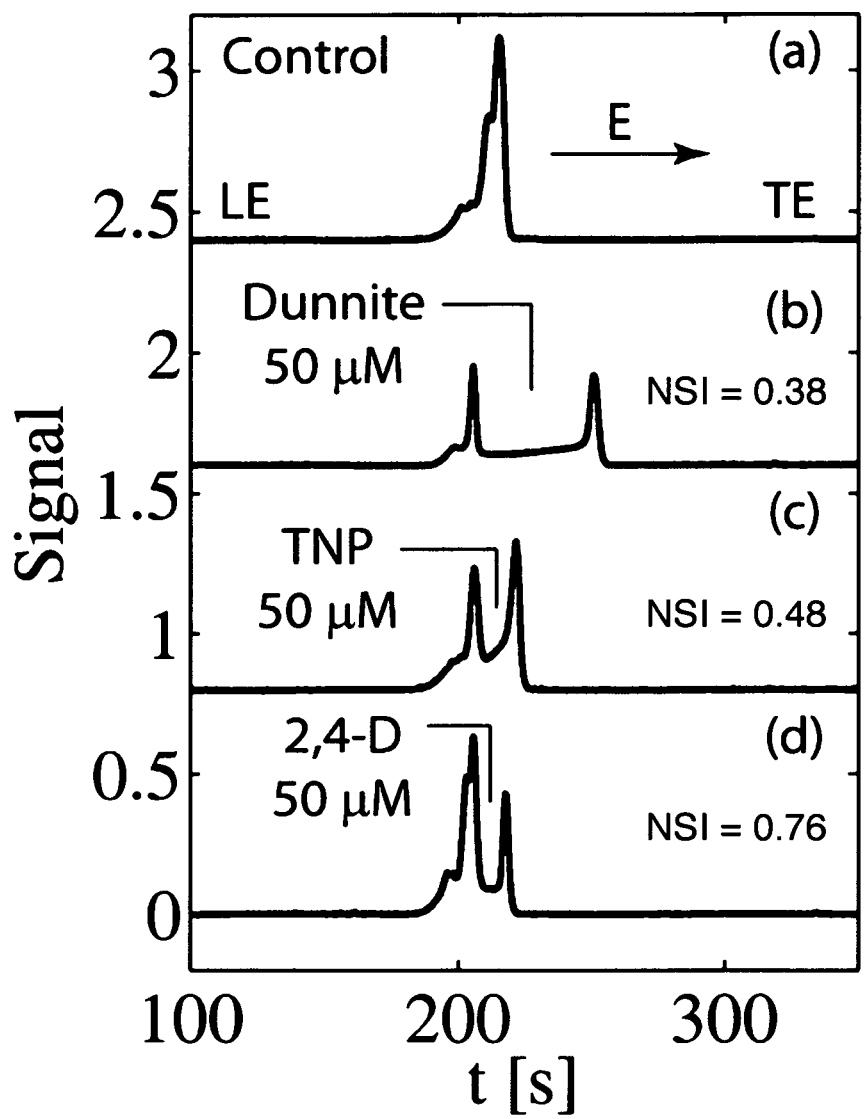
FIG. 11 shows indirect detection of an explosive and an endocrine disrupter in river water using an FCA assay.

FIG. 11 shows indirect detection of explosives and an endocrine disruptor in river water, with no sample preparation steps. The signal in (a) shows a negative control (no analytes present). The fluorescent ampholytes form a contiguous (yet non-uniform signal). (b) 50 µM of ammonium 2,4,6-trinitrophenolate (Dunnite) were added to the TE reservoir. The analyte displaces a subset of the fluorophores and creates a detectable gap in the signal. (c), (d) Indirect detection of 2,4,6-trinitrophenol (TNP) and 2,4-Dichlorophenoxyacetic acid (2,4-D) respectively. LE is 10 mM hydrochloric acid, TE is 10 µM tricine and the counterion is 20 mM bis-tris. The LE reservoir was titrated to a pH of 6.9 with 5 µM of NaOH. 1 µM of ZOOM® 3-10 labeled with Alexa Fluor 647 were mixed in the TE. 204 V was applied along a 23 mm channel with a 17:1 cross section area reduction positioned 48% of the way along its length from the TE reservoir (the detection region is 17 mm from the channel inlet where samples are introduced).

We applied our method to detect indirectly ionic water soluble explosives, ammonium 2,4,6-trinitrophenolate (Dunnite) and 2,4,6-trinitrophenol (TNP), and a herbicide, dichlorophenoxyacetic acid (2,4-D). 2,4-D is the world's most common herbicide (third-most common in the US) and has, importantly, been implicated as an endocrine disruptor in potable water. We spiked the samples in river water (Vernal Falls, Merced River, Yosemite Valley, Calif., USA) and focused, separated, and detected with no additional sample preparation. FIG. 11a shows a control run performed using river water with no added analytes. FIGS. 11b-d respectively show the detection of 50 µM Dunnite, 50 µM TNP, and 50 µM 2,4-D, spiked in the river water. Each of the analytes focuses at a highly specific location determined by its effective mobility, displacing a subset of the CAs and creating a gap (or "valley") in the fluorescent signal. The amount of displaced carrier ampholytes can be used for identification of an analyte. In the figure, we indicate the value of the normalized signal intensity (NSI) which can be used to analyze and identify chemical species as described above.

B5) Analyte Identification Conclusions

We demonstrated that our fluorescent carrier ampholyte technique can be used to estimate the fully ionized mobility and dissociation constant of detected analyte ions. These physicochemical properties can be used to identify analytes with little or no a priori knowledge, short analysis time, and no sample preparation.

We have shown that the fraction of fluorescent carrier ampholytes displaced by ITP focused analytes can be quantified by integration and appropriate normalization of the fluorescence signal. To this end, we defined and presented a method for calculating a normalized value, NSI, defined as the signal integral from LE to analyte normalized by the total signal integral (from LE to TE). NSI is proportional to the amount of CA focused between the LE and analyte. We showed that the NSI of an ionic analyte is monotonic with the effective mobility it acquires in its respective ITP zone. We used this property to construct two calibration curves, based on two different LE buffers, which can be used to convert experimentally measured NSI values to effective mobility values. Once effective mobilities are obtained, we use an ITP theory (and associated effective mobility contours versus fully ionized mobility and pKa) to retrieve the analyte ion's fully ionized mobility and pKa. We demonstrated this process for the detection and identification of 2-nitrophenol and 2,4,6-trichlorophenol and obtained respective dissociation constants in good agreement with published values.

There are several possibilities for further improving this technique. First, additional calibrant analytes can be used to improve the accuracy of interpolation (e.g., as in FIG. 9). As shown here, different approximations of the calibration curves (i.e. linear interpolation vs. quadratic fit) can result in differences in extracted pKa values of approximately 5% (e.g., pKa 7 with linear interpolation vs. pKa 6.7 with quadratic best-fit). The results clearly depend on the resolution of the calibration curve, and we expect that additional calibration points (i.e. performing the assay on additional species whose mobility and pKa are known) should improve the accuracy. Second, LE buffers can be selected to optimize the shape of the mobility contour map (as in FIG. 10). For example, LE combinations can be chosen to increase the angles between intersecting contour lines, thus reducing the error associated with the estimates of pKa and fully ionized mobility given inaccuracies in effective mobility measurement. Calibrant analytes can be added to actual samples as an internal standard and simultaneous calibration in a single experiment. Two simultaneous ITP runs in the same chip using a common TE reservoir can be performed, to reduce the analysis time and sample variability between runs. As indicated above, the FCA assay can be integrated in a self contained hand-held device, thereby enabling low-cost and portable identification of analytes in point of service settings.

The invention claimed is:

1. An analysis method comprising:
   providing a sample including one or more analytes to be analyzed;
   adding a carrier ampholyte (CA) mixture to the sample, wherein the carrier ampholyte mixture includes 10 or more labeled species having a range of isoelectric points;
   performing isotachophoresis (ITP) of the combined CA mixture and sample to provide an ITP separation;
   measuring one or more signals from the labeled amphoteric species in the ITP separation to provide measured CA signals;
   detecting and/or identifying at least one of the one or more analytes based on analysis of the measured CA signals.

2. The method of claim 1, wherein the labeled species of the CA mixture are amphoteric species.

3. The method of claim 1, wherein the labeled species of the CA mixture have isoelectric points covering a range from pHmin to pHmax, and wherein pHmax−pHmin≥1.

4. The method of claim 1, wherein the detailed composition of the CA mixture is not known.

5. The method of claim 1, wherein the labeled species in the CA mixture are labeled with one or more labels selected from the group consisting of: fluorescent labels, electrochemical labels, UV absorbance labels, thermo-optical labels and radioactive labels.

6. The method of claim 1, wherein the labeled species of the CA mixture are anionic and have effective electrophoretic mobilities covering a range from µmin to µmax, wherein µmax−µmin≥$10^{-8}$ m²/(Vs).

7. The method of claim 1, wherein the labeled species of the CA mixture are cationic and have effective electrophoretic mobilities covering a range from µmin to µmax, wherein $\mu_{max} - \mu_{min} \geq 10^{-8}$ m²/(Vs).

8. The method of claim 1, wherein the analytes are not labeled.

9. The method of claim 1, wherein the detecting and/or identifying at least one of the one or more analytes does not rely on any measured signal directly from the analytes.

10. The method of claim 1, wherein the ITP separation is an anionic ITP separation or a cationic ITP separation.

11. The method of claim 1, wherein the ITP separation is performed in a channel having a first section connected to a second section, wherein the first section has a substantially larger cross-section area than the second section, and wherein the measured CA signals are measured at one or more points in the second section.

12. The method of claim 1, further comprising adding one or more species having known properties to the sample to provide an internal reference for effective mobility of the one or more analytes.

13. The method of claim 1, wherein measurement of multiple samples is provided by parallel measurements in multiple channels.

14. The method of claim 1, further comprising computing a normalized signal integral (NSI) for analyte identification.

15. The method of claim 14, further comprising generating an empirical calibration relating the normalized signal integral to effective mobility.

16. The method of claim 15, further comprising performing two or more measurements of effective mobility from NSI data for a single analyte with different ITP conditions, and determining a fully ionized mobility and pKa of the single analyte from the two or more measurements of effective mobility.

17. An analysis method comprising performing the method of claim 1 for several distinct pH values to provide a 2-D pattern of CA signals vs. pH.

18. The method of claim 17, further comprising identifying analytes from the 2-D pattern of CA signals vs. pH.

19. The method of claim 17, wherein the 2-D pattern of CA signals vs. pH is provided by sequential measurements in a single channel.

20. The method of claim 17, wherein the 2-D pattern of CA signals vs. pH is provided by parallel measurements in multiple channels.

* * * * *